United States Patent [19]

Kuhn et al.

[11] Patent Number: 4,996,348

[45] Date of Patent: Feb. 26, 1991

[54] N-ALKENOYL ENAMIDES, THEIR PREPARATION AND THE USE THEREOF

[75] Inventors: Martin Kuhn, Dornach, Switzerland; Philippe Ouziel, Riedisheim, France

[73] Assignee: Ciba-Geigy Corporation, Ardsley, N.Y.

[21] Appl. No.: 221,405

[22] Filed: Jul. 19, 1988

[30] Foreign Application Priority Data

Jul. 29, 1987 [CH] Switzerland ............... 2911/87

[51] Int. Cl.$^5$ .............. C07C 255/07; C07C 255/09; C07C 255/10; C07C 255/34
[52] U.S. Cl. ...................... 558/445; 558/404; 558/405; 560/171; 560/172; 564/153; 564/159; 564/160; 564/204; 564/207
[58] Field of Search ............ 564/204, 207; 558/405, 558/445, 404

[56] References Cited

U.S. PATENT DOCUMENTS

| | | | |
|---|---|---|---|
| 3,657,340 | 4/1972 | Johnson et al. | 260/557 R |
| 4,276,288 | 6/1981 | Etschenberg et al. | 514/19 |
| 4,310,517 | 1/1982 | Etschenberg et al. | 514/17 |

FOREIGN PATENT DOCUMENTS 0218089 4/1987 European Pat. Off.
2718552 11/1986 Fed. Rep. of Germany.

OTHER PUBLICATIONS

Derwent Abstract 87-080763/12.
Derwent Abstract 77-81488y/46.
L. Claisen, Liebigs Ann. Chem., 297, pp. 16–32 (1987).
M. Waison, Chapter 2: Per-Compounds and Per-Salts in Polymer Processes, 161 et seq. (1980).

Primary Examiner—Joseph Paul Brust
Attorney, Agent, or Firm—Kevin T. Mansfield; Edward McC. Roberts

[57] ABSTRACT

Novel N-alkenoyl enamide of the formula

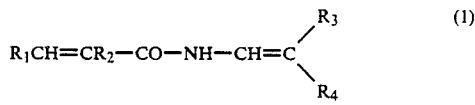

wherein
$R_1$ is hydrogen or methyl,
$R_2$ is hydrogen, $C_1$-$C_4$alkyl or halogen, and
$R_3$ and $R_4$ are each independently of the other $C_1$-$C_4$alkanolyl, $C_1$-$C_{18}$alkoxycarbonyl, benzoyl, phenyl, cyano or carbamoyl, and $R_4$ can also be hydrogen, are used for photocrosslinkable compositions suitable for use in photographic solutions, as UV absorbers and as textile finishing agents.

4 Claims, No Drawings

N-ALKENOYL ENAMIDES, THEIR PREPARATION AND THE USE THEREOF

The present invention relates to novel N-alkenoyl enamides, to a process for their preparation, to the use thereof for the synthesis of novel polymers, and to the use of the novel polymers in radiation curable materials, as UV absorbers and as textile finishing agents.

N-Alkenoyl enamides are known, for example from German Offenlegungsschrift 2 718 552. They can be used for the preparation of acylamines, of polymers containing amino groups, or of amino acid.

There have now been found novel alkenoyl enamides which can be used for the preparation of polymers which can, in turn, be used in radiation curable materials, as UV absorbers and as textile finishing agents.

Specifically, the present invention relates to novel N-alkenoyl enamides of formula $$R_1CH=CR_2-CO-NH-CH=C{\overset{\displaystyle R_3}{\underset{\displaystyle R_4}{}}} \quad (1)$$

wherein
$R_1$ is hydrogen or methyl,
$R_2$ is hydrogen, $C_1$-$C_4$alkyl or halogen, and
$R_3$ and $R_4$ are each independelty of the other $C_1$-$C_4$ alkanoyl, $C_1$-$C_{18}$alkoxycarbonyl, benzoyl, phenyl, cyano or carbamoyl, and $R_4$ can also be hydrogen.

Preferred compounds of formula (1) are those wherein $R_2$ is hydrogen, methyl or chlorine, and $R_3$ and $R_4$ are each independently of the other acetyl, $C_1$-$C_{18}$alkoxycarbonyl, benzoyl, phenyl, cyano or carbamoyl, and $R_4$ can also be hydrogen.

The most preferred compounds of formula (1) are those wherein $R_2$ is hydrogen or methyl, and $R_3$ and $R_4$ are each independently of the other acetyl or ethoxycarbonyl.

The N-alkenoyl enamides of this invention can be obtained economically and in good yield.

The invention thus also relates to a process for the preparation of the N-alkenoyl enamides of formula (1), which comprises reacting an alkenamide of formula $$R_1-CH=CR_2-CO-NH_2 \quad (2)$$

wherein $R_1$ and $R_2$ are as defined above, with an enol ether of formula $$RO-CH=C{\overset{\displaystyle R_3}{\underset{\displaystyle R_4}{}}} \quad (3)$$

wherein R is $C_1$-$C_4$alkyl and $R_3$ and $R_4$ are as defined above, in the presence of a catalyst for the removal of the alkanol (ROH).

A suitable catalyst for the removal of the alkanol ROH is, in particular, phenothiazine, which acts simultaneously as polymerisation inhibitor in the temperature range from 130°-200° C., preferably from 140°-190° C.

The alkenamides of formula (2) are known compounds.

Some of the enol ethers of formula (3) are known, for example from U.S. patent specification 2,824,121. The novel enol ethers can be prepared by the process disclosed in this U.S. patent specification.

Examples of suitable enol ethers of formula (3) are compounds of formula $$RO-CH=C{\overset{\displaystyle R_3}{\underset{\displaystyle R_4}{}}}$$

wherein R, $R_3$ and $R_4$ have the meanings given in Table I.

TABLE I

| No. | R | $R_3$ | $R_4$ | b.p. °C./mbar | m.p. °C. |
|-----|---|-------|-------|---------------|----------|
| a | $CH_3$ | $CH_3CO$ | $CH_3CO$ | 130–132/31.2 | |
| b | $C_2H_5$ | $CH_3CO$ | $CH_3CO$ | 136/28.6 | |
| c | $CH_3$ | $CH_3CO$ | $C_2H_5OOC$ | 142/28.6 | |
| d | $C_2H_5$ | $CH_3CO$ | $C_2H_5OOC$ | 137/20.8 | |
| e | $CH_3$ | $CH_3OOC$ | $CH_3OOC$ | 104/0.5 | 39.8 |
| f | $CH_3$ | CN | $C_2H_5OOC$ | 105–108/0.03 | 92.3–94.5 |
| g | $CH_3$ | $CH_3CO$ | H | 60–61/23.4 | |
| h | $C_2H_5$ | CN | $C_2H_5OOC$ | | 49–51 |
| i | $C_2H_5$ | CN | CN | | 65–67 |
| j | $C_2H_5$ | $C_2H_5OOC$ | $C_2H_5OOC$ | 135–140/13.0 | |
| k | $C_2H_5$ | CN | H | 188–190/1.3 | |

The N-alkenoyl enamides of formula (I) can also be prepared by reacting an amine of formula $$H_2N-CH=C{\overset{\displaystyle R_3}{\underset{\displaystyle R_4}{}}} \quad (4)$$

wherein $R_3$ and $R_4$ are as defined above, with an acyl halide of formula $$R_1-CH=CR_2-CO-Hal \quad (5)$$

wherein $R_1$ and $R_2$ are as defined above and Hal is bromine or, preferably, chlorine, in the presence of an acid acceptor. This procedure is described as analogy process by L. Claisen, Liebigs Ann. Chem. 297 (1897), 16 to 32.

Suitable amines of formula (4) are, for example, compounds in which $R_3$ and $R_4$ have the following meanings:

TABLE II

| No. | $R_3$ | $R_4$ | m.p. °C. | b.p. °C./mbar |
|-----|-------|-------|----------|---------------|
| a | CN | CN | 127 | |
| b | CN | $COOC_2H_5$ | 130 | |
| c | $COCH_3$ | $COCH_3$ | 144 | |
| d | $COCH_3$ | $COOC_2H_5$ | 47 | |
| e | $COOCH_3$ | $COOCH_3$ | 125 | |
| f | $COCH_3$ | H | | 46/0.06 |
| g | CN | H | | |

Examples of suitable acyl halides of formula (5) are the chlorides of acrylic, methacrylic or crotonic acid.

The reaction is exothermic, frequently even at room temperature, with formation of hydrochloric acid.

The N-alkenoyl enamides of formula (1) can be used for the synthesis of polymers which contain 100-1 mol % of structural units of formula I and 0–99 mol % of structural units of formula II

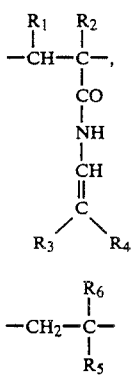

wherein $R_1$, $R_2$, $R_3$ and $R_4$ are as defined above, $R_5$ is carboxy, $C_1$–$C_{18}$alkoxycarbonyl, N,N-$C_1$–$C_4$dialkylamino-$C_1$–$C_4$alkylcarbamoyl, cyano, formyl, N,N-$C_1$–$C_4$dialkylamino-$C_1$–$C_4$alkoxycarbonyl, $C_1$–$C_4$alkanoyloxy, unsubstituted or substituted carbamoyl, 1-pyrrolidonyl, 1-imidazolyl, 2- or 4-pyridinyl or phenyl, and $R_6$ is hydrogen or methyl, by subjecting them to a radical-induced polymerisation at elevated temperature, in the presence of an organic inert solvent and a polymerization initiator.

Suitable organic inert solvents are protic and aprotic solvents, for example tetrahydrofuran, dioxane, toluene, xylene, ethyl acetate, butyl acetate, 4-butyrolactone, acetone, diethyl ketone, methyl ethyl ketone, methyl isobutyl ketone, methyl glycol acetate, ethyl glycol acetate, dimethyl formamide, dimethyl acetamide and N-methylpyrrolidone.

Suitable polymerisation initiators are compounds containing bonds which can readily severed thermally by homolysis, for example the hydroperoxides, peroxides and per esters described by M. Warson, Chandler, Braintree, England "Per-Compounds and Per-Salts in Polymer Processes", (1980), 161 et seq. (C.A. 93, (1980) 205312 v), as well as aliphatic azo compounds such as azobisisobutyronitrile, 4,4'-azobis(4-cyanovalerate) and the like.

The polymerisation is carried out in the temperature range from 60° to 100° C.

The copolymer unit of formula II is suitably a vinyl compound such as acrylic or methacrylic acid, an alkyl ester or alkylaminoalkylamide of acrylic or methacrylic acid, styrene, a N-$C_1$–$C_4$dialkylamino-$C_1$–$C_4$alkyl ester of acrylic or methacrylic acid, an acrylamide or a methacrylamide, a N-substituted acrylamide or methacrylamide, a N-$C_1$–$C_4$dialkylamino-$C_1$–$C_4$alkylacrylamide or -methacrylamide, acrylonitrile or methacrylonitrile, acrolein, a derivative of acrolein, vinyl acetate, 1-vinylpyrrolidone, 1-vinylimidazole and 2- or 4-vinylpyridine.

The polymers obtainable according to this invention therefore constitute a further object of the invention. They conform to formulae I and II above.

These polymers, i.e. the copolymers and homopolymers, can be used in photocrosslinkable compositions for producing images, for example in photographic solutions, for producing relief patterns in commercial printing, for producing resists of high resolution for use in microelectronics, in UV curable coatings and coating compositions of high resistance to solvents and temperature, and, in view of the fact that said polymers absorb in the wavelength range from 270–300 nm, as UV absorbers in UV absorbing sheets such as sandwich glasses for motor vehicles and constructional glazing and in protective sheets for greenhouses, or as textile finishing agents for imparting specific properties such as crease resistance and water resistance.

The copolymers make it possible in particular to produce heat-resistant resist images of good resolution, as they normally have quite high glass transition temperatures ($T_g$) in conjunction with good mechanical properties.

The following Examples illustrate the invention in more detail.

PREPARATION OF THE MONOMERS

Example 1

A round bottom flask is charged with 252 g of ethoxymethylene acetylacetone, 114.7 g of acrylamide and 1 g of phenothiazine and the mixture is heated, with stirring, to 160° C. Distillation of eliminated ethanol commences at 140° C. After distillation of 64.3 g of ethanol, the reaction is discontinued (by cooling) and the monomer is distilled off.

The resultant product (251 g) is recrystallised from 220 ml of isopropanol, to give 188 g (64% of theory) of the monomer of formula

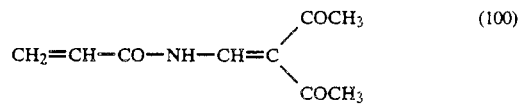

which has a melting point of 58.6°–59.8° C.

Example 2

A round bottom flask is charged with 377.7 g of ethyl ethoxymethylene acetoacetate, 144.2 g acrylamide and 5 g of phenothiazine and the mixture is heated to 160° C. After distillation of 84 g of ethanol, the reaction is discontinued (by cooling) and the monomer is distilled off. Recristallisation from 300 ml of isopropanol gives 275 g of the monomer of formula

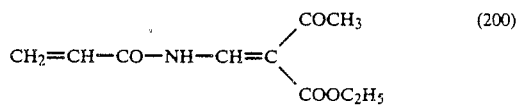

with a melting point of 65.2°–66.8° C.

Example 3

Following the procedure of Example 1, 350.5 g of ethoxymethylene diethyl malonate, 138.5 g acrylamide and 4 g of phenothiazine are reacted at 190° C. After distillation of 60 g of ethanol, the monomer is distilled off and recrystallised from 100 ml of cyclohexane, to give 90 g (23% of theory) of the monomer of formula

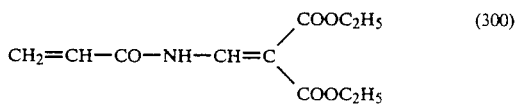

which, after further distillation, has a melting point of 46.2°–47.2° C.

Example 4

Following the procedure of Example 1, 217.6 g ethyl ethoxymethylene acetoacetate, 99.5 g of methacrylamide and 2.5 g of phenothiazine are reacted at 155° C., to give 171 g (65% of theory) of the monomer of formula

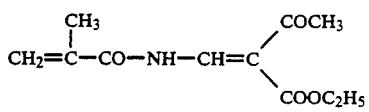
(400)

with a melting point of 25.5° C.

The following monomers are obtained in corresponding manner:

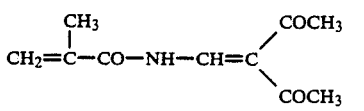
(401)

m.p. 46.8–47.9° C.

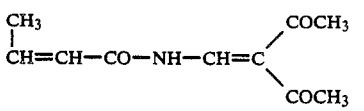
(402)

m.p. 33.2–34.7° C.

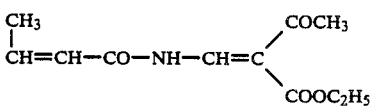
(403)

m.p. 90.4–91.9° C.

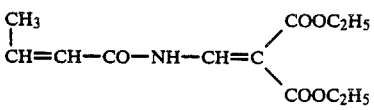
(404)

m.p. 68.5–69.8° C.

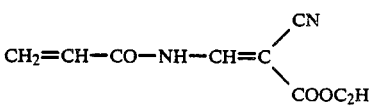
(405)

m.p. 66.3–68.5° C.

PREPARATION OF THE POLYMERS

Example 5:

A reaction vessel equipped with stirrer, cooler and thermometer is charged with 18.75 g of the monomer of formula (200), 0.02 g of tert-butyl-peroxy-2-ethylhexanoate and 28 g of dioxane. After blanketing with nitrogen for 10 minutes, the mixture is heated to 82° C. From 77° C. polymerisation commences with evolution of heat and slight turbidity occurs after 90 minutes. After 2 hours the reaction is discontinued by cooling and the slightly turbid, viscous solution is diluted with dioxane. The homopolymer is precipitated by pouring the solution into ethanol, affording 171 g (91% of theory) of the homopolymer with a reduced viscosity of 0.32 dl/g in dioxane (c=0.5 g/v).

Example 6:

The procedure of Example 5 is repeated, using 39 g of the monomer of formula (100), 0.2 g of didodecanoyl peroxide and 47 ml of tetrahydrofuran. After expelling the air with nitrogen, the mixture is heated for 20 hours to 67° C., with stirring. The solution becomes slightly turbid and viscous. The solution is then cooled and poured into ethyl alcohol to precipitate the homopolymer. The precipitate is then dried, to give the homopolymer in a yield of 38.2 g (97.4% of theory). It has a reduced viscosity of 0.10 dl/g in acetone (c=0.5 g/v).

Example 7:

The procedure of Example 5 is repeated, using 25.4 g of the monomer of formula (100), 6 g of ethyl acrylate and 0.1 g of tert-butylperoxy-2-ethylhexanoate and 90 ml of ethyl acetate. After expelling the air with nitrogen, the mixture is heated for 5 hours to 76° C. with stirring. The homopolymer is precipitated by pouring the cooled solution into ethyl alcohol. The precipitate is dried, affording 28.8 g of a polymer consisting of 70 mol % of the monomer of formula (100) and 30 mol % of ethyl acrylate, and having a reduced viscosity of 0.41 dl/g in acetone (c=0.5 g/v).

Example 8:

The procedure of Example 5 is repeated, using 16.5 g of the monomer of formula (401), 1.1 g of acrylic acid, 0.04 g of tert-butylperoxy-2-ethylhexanoate and 26 g of dioxane. After expelling the air with nitrogen, the mixture is heated to 82° C. for 3¼ hours, with stirring. The solution is then cooled and poured into ethanol to precipitate the polymer. The precipitate is dried, affording 14 g (79.9% of theory) of a polymer consisting of 84.6 mol % of the monomer of formula (401) and 15.4 mol % of acrylic acid. The polymer has a reduced viscosity of 0.28 dl/g in acetone (c=0.5 g/v).

The following polymers are obtained in corresponding manner from the monomer of formula

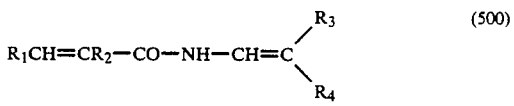
(500)

wherein $R_1$ is hydrogen and $R_3$ and $R_4$ are —$COCH_3$ and $R_2$ has the meanings given in Table I, and, where indicated, from the comonomer acrylic acid (A), ethyl acrylate (B) or styrene (C):

TABLE I

| Polymer | $R_2$ | Comonomer | Monomer (mol %) | Comonomer (mol %) | Initiator (mol %) | Yield (%) | $\eta_{red}$* (g/dl) |
|---|---|---|---|---|---|---|---|
| 1 | H | — | 99.90 | — | 0.1 | 94 | 0.79 |
| 2 | H | — | 99.90 | — | 0.1 | 78.3 | 0.23 |
| 3 | H | B | 49.90 | 49.82 | 0.27 | 92 | 0.99 |
| 4 | H | B | 89.75 | 9.94 | 0.3 | 96.5 | 0.36 |
| 5 | H | A | 84.68 | 15.20 | 0.11 | 88.5 | 0.22 |
| 6 | H | C | 49.77 | 49.81 | 0.41 | 90 | 0.30 |
| 7 | $CH_3$ | — | 99.80 | — | 0.20 | 72 | 0.30 |

*measured in acetone at c = 0.5% g/v

Solvents for the polymerisation ethyl acetate for polymers 1, 3 and 4
dioxane for polymers 2, 5 and 7 toluene for polymer 6.

Example 9

A reactor equipped with stirrer, cooler and thermometer is charged with 30 g of the monomer of formula (200), 14.2 g of ethyl acrylate. 0.15 g of tert-butyl-peroxy-2-ethylhexanoate and 100 ml of ethyl acetate. The mixture is heated for 4 hours to 75° C., with stirring. The solvent is then stripped off and the copolymer is taken up in acetone. The polymer is precipitated by pouring the solution into water. Yield: 41.1 g (92.7% of theory) of copolymer consisting of 50 mol % of units of the monomer of formula (200) and 50 mol % of ethyl acrylate.

Example 10

The procedure of Example 9 is repeated, using 23.8 g of the monomer of formula (200), 3.4 g of dimethylaminopropyl methacrylamide, 0.06 g of tert-butyl-peroxy-2-ethylhexanoate and 40 g of dioxane. The mixture is heated for 5 hours to 83° C., with stirring. After addition of a further 0.06 g of tert-butyl-peroxy-2-ethylhexanoate, polymerisation is carried out for 14 hours at 83° C. The cooled reaction solution is poured into ethyl alcohol to precipitate the copolymer. Yield: 11.2 g (41% of theory) of copolymer consisting of 85 mol % of units of formula (200) and 15 mol % of dimethylaminopropyl methacrylamide.

The following monomers are prepared in corresponding manner from the monomer of formula (500), wherein $R_1$ is hydrogen, $R_3$ is —COCH$_3$, $R_4$ is —COOC$_2$H$_5$ and $R_2$ has the meanings given in Table II, and, where indicated, from the comonomer (A) or (C):

TABLE II

| Polymer | $R_2$ | Comonomer | Monomer (mol %) | Comonomer (mol %) | Initiator (mol %) | Yield (%) | $\eta_{red}$* (g/dl) |
|---|---|---|---|---|---|---|---|
| 8 | H | — | 99.76 | — | 0.24 | 95.6 | 0.107 |
| 9 | H | — | 99.81 | — | 0.19 | 95.8 | 0.416 |
| 10 | H | — | 99.90 | — | 0.10 | 91 | 0.29 |
| 11 | H | C | 49.68 | 49.84 | 0.48 | 93.6 | — |
| 12 | H | A | 84.62 | 15.26 | 0.11 | 88 | 0.34 |
| 13 | CH$_3$ | — | 99.11 | — | 0.89 | 85.6 | 0.14 |
| 14 | CH$_3$ | — | 99.80 | — | 0.20 | 72 | 0.44 |
| 15 | CH$_3$ | A | 84.53 | 15.29 | 0.18 | 78.6 | 0.32 |

*measured in acetone at c = 0.5% g/v

Solvents for the polymerisation tetrahydrofuran for polymer 8
ethyl acetate for polymers 9 and 13
dioxane for polymers 10, 12, 14 and 15
toluene for polymer 11.

Example 11

The procedure of Example 9 is repeated, using 20.4 g of the monomer of formula (300), 1.1 g acrylic acid, 0.04 g of tert-butylperoxy-2-ethylhexanoate and 32 g of dioxane. The mixture is heated for 2½ hours to 82° C., with stirring. The copolymer is precipitated by pouring the cooled solution into water, to give 20.5 g (95.3% of theory) of a copolymer consisting of 84.6 mol % of the monomer of formula (300) and 15.4 mol % of acrylic acid, and having a reduced viscosity of 0.3 dl/g in acetone (c=0,5% g/v).

The following homopolymers are obtained in corresponding manner: from the monomer of formula (500), wherein $R_1$ and $R_2$ are hydrogen and $R_3$ and $R_4$ are —COOC$_2$H$_5$:

TABLE III

| Polymer | Comonomer | Monomer (mol %) | Comonomer (mol %) | Initiator (mol %) | Yield (%) | $\eta_{red}$* (g/dl) |
|---|---|---|---|---|---|---|
| 16 | — | 99.74 | — | 0.26 | 100 | 0.100 |
| 17 | — | 99.66 | — | 0.34 | 92.2 | 0.702 |
| 18 | — | 99.80 | — | 0.20 | 96.7 | 0.313 |

*measured in acetone at c = 0.5% g/v

Solvents for the polymerisation tetrahydrofuran for polymer 16
ethyl acetate for polymer 17
dioxane for polymer 18 from the monomer of formula (500), wherein $R_1$ is methyl, $R_2$ is hydrogen and $R_3$ and $R_4$ have the meanings given in Table IV, and from the comonomer vinyl acetete (E):

TABLE IV

| Polymer | $R_3$ | $R_4$ | Comonomer | Monomer (mol %) | Comonomer (mol %) | Initiator (mol %) | Yield (%) | $\eta_{red}$* (g/dl) |
|---|---|---|---|---|---|---|---|---|
| 19 | CH$_3$—CH— | C$_2$H$_5$—COO— | E | 49.88 | 49.60 | 0.67 | 90 | 0.27 |
| 20 | C$_2$H$_5$—COO— | C$_2$H$_5$—COO— | E | 49.81 | 49.67 | 0.68 | 61 | 0.08 |
| 21 | CH$_3$—CO— | CH$_3$—CO— | E | 49.83 | 49.64 | 1.2 | 31 | 0.07 |

*measured in acetone at c = 0.5% g/V

Solvent for the polymerisation: dioxane

Example 12

A 50 ml surface ground flask equipped with stirrer, thermometer and reflux condenser (exit blocked by a bubble counter attachment filled with light paraffin) is charged with 15.0 g of acrylamidomethylene acetylacetone, 3.8 g of N-tert-butylacrylamide, 2.7 g of acrylic acid, 1.0 g of tert-butylperoctoate (10% in dioxane) and 31.0 g of dioxane. The monomer content of the solution is 40.2% by weight. After cautious blanketing with nitrogen, the batch is heated to 80° C., with stirring.

The ensuing polymerisation is strongly exothermic, the temperature of the reaction mixture rising to 105° C. After 5 minutes the reaction mixture is diluted with 5 ml of dioxane and the polymerisation is allowed to go to completion for 5 hours at 80° C. The resultant highly viscous, clear solution is further diluted with dioxane and poured into water to precipitate the polymer. The precipitate is dried, affording 20.6 g (95.8% of theory) of a colourless copolymer with a softening point of >200° C. and a reduced viscosity of 0.73 dl/g in dioxane.

Example 13

The procedure of Example 12 is repeated, using 15.0 g of acrylamidomethylene acetylacetone, 3.5 g of N-methyl-N-vinylacetamide, 0.7 g of tert-butyl peroctoate (10% in dioxane) and 27.0 g of dioxane. The monomer content of the solution is 40% by weight. After cautious blanketing with $N_2$, the batch is heated to 80° C., with stirring. The ensuing polymerisation is strongly exothermic, the temperature rising to 98° C. The reaction mixture is diluted with 20 ml of dioxane and the polymerisation is allowed to go to completion for 5 hours at 82° C. The resultant clear, slightly yellowish viscous solution is further diluted with dioxane and poured into water to precipitate the polymer. The precipitate is dried, affording 17.8 g (96.2% of theory) of an almost colourless copolymer with a softening point of >200° C. After drying, the product loses its solubility in dioxane and DMA and is then only highly swellable.

Example 14

The procedure of Example 12 is repeated, using 10.0 g of acrylamidomethylene acetylacetone, 2.9 g of styrene, 2.8 g of ethyl acrylate, 0.7 g of tert-butyl peroctoate (10% in dioxane) and 23.0 g of dioxane. The monomer content is 39.9% by weight. After cautious blanketing with $N_2$, the batch is heated to 80° C., with stirring. This temperature is kept for 5 hours and the batch is diluted with dioxane and poured into water to precipitate the polymer. Yield: 15.0 g (95.5% of theory) of a colourless copolymer with a softening point of 158° C. and a reduced viscosity of 0.72 dl/g in dioxane.

Example 15

The procedure of Example 12 is repeated, using 11.1 g of ethyl acrylamidomethylene acetoacetate, 0.85 g of acrylonitrile, 1.3 g of N-vinylpyrrolid-2-one, 0.4 g of tert-butyl peroctoate (10% in dioxane) and 24.0 g of dioxane. After cautious blanketing with $N_2$, the batch is heated to 80° C., with stirring. After the exothermic polymerisation has subsided, the temperature is kept for 5 hours at 80° C. and the clear, highly viscous solution is further diluted with dioxane and poured into water to precipitate the polymer. The precipitate is dried, affording 12.2 g (92% of theory) of a colourless copolymer with a softening point of 170° C. and a reduced viscosity of 0.93 dl/g in dioxane.

Example 16

The procedure of Example 12 is repeated, using 13.0 g of ethyl acrylamidomethylene acetoacetate, 2.0 g of N-methoxymethylmethylacrylamide, 0.4 g of tert-butyl peroctoate (10% in dioxane) and 27.0 g of dioxane. The monomer content of the solution is 35.4% by weight. After blanketing with nitrogen, the mixture is heated to 80° C. After the exothermic polymerisation has subsided, the temperature is kept at 80° C. for 5 hours and the batch is diluted with dioxane and poured into water to precipitate the polymer. The precipitate is dried, affording 14.4 g (96% of theory) of a colourless copolymer which has a softening point of 158° C. and a reduced viscosity of 0.3 dl/g in dioxane.

Example 17

The procedure of Example 12 is repeated, using 13.0 g of ethyl acrylamidomethylene acetoacetate, 1.3 g of vinyl acetate, 0.4 g of tert-butyl perocotate (10% in dioxane) and 47 g of dioxane. The monomer content of the solution is 23.2% by weight. After cautious blanketing with $N_2$, polymerisation is carried out for 2 hours at 80° C. The resultant clear, viscous solution is diluted with dioxane and then poured into water to precipitate the polymer. The precipitate is dried, affording 13.2 g (92.3% of theory) of a colourless copolymer with a softening point of 165° C. and a reduced viscosity of 0.26 dl/g in dioxane.

Example 18

The procedure of Example 12 is repeated, using 20.0 g of acrylamidomethylene acetylacetone, 10.7 g of stearyl methacrylate, 2.0 g of N-tert-butylacrylamide, 0.1 g of tert-butyl peroctoate and 60 g of dioxane. The monomer content is 35% by weight. After cautious blanketing with $N_2$, the batch is heated to 80° C., with stirring. This temperature is kept for 4½ hours, then the clear, viscous, slightly yellowish solution is diluted with 50 ml of dioxane and poured into water to precipitate the polymer. Yield: 31.9 g (97.2% of theory) of a colourless copolymer with a softening point of 97° C. and a reduced viscosity of 0.38 dl/g in dioxane.

Example 19

12.0 g of acrylamidomethylene acetylacetone, 0.9 g of acrylonitrile, 28.0 g of stearyl methacrylate, 0.1 g of tert-butyl peroctoate and 65 ml of dioxane are weighed together into a reactor. The monomer content is 38% by weight. After cautious blanketing with nitrogen, the batch is heated to 80° C., with stirring, and polymerisation is carried out for 5 hours at this temperature. The clear, viscous, yellow solution is diluted with further dioxane and poured into 2 litres of water to precipitate the polymer. Yield: 40 g (97.5% of theory) of a colourless copolymer with a softening point of 55° C. and a reduced viscosity of 0.42 dl/g in dioxane.

Example 20

12.0 g of acrylamidomethylene acetylacetone, 1.8 g of acrylonitrile, 22.4 g of stearyl methacrylate, 0.1 g of tert-butyl peroctoate and 60 ml of dioxane are weighed together into a reactor. The monomer content is 37% by weight. After cautious blanketing with nitrogen, the batch is heated to 80° C., with stirring, and polymerisation is carried out for 5 hours at this temperature. The clear, viscous, yellow solution is diluted with further dioxane and poured into 2 litres of water to precipitate the polymer. Yield: 34.8 g (96% of theory) of a colourless copolymer with a softening point of 60° C. and a reduced viscosity of 0.55 dl/g in dioxane.

USE EXAMPLES

Example 21

Coating solution

| | |
|---|---|
| polymer 3 of Table I | 1.5 g |
| 4-butyrolactone | 10.0 g |
| wetting agent based on perfluoro-carboxylic acid, e.g. Fluorad ® FC 430 (ex 3M) | 0.001 g |

The solution is coated with a coating knife to a film thickness of 12μ on to a copper laminated epoxy resin plate. The coating is dried for 2¼ hours at 60° C., a photomask (Stouffer wedge) is laid on the plate, which is irradiated for 300 seconds with a 1000 W UV lamp from a distance of 18 cm. The plate is then developed. The last clearly reproduced step was 9.

Example 22

Cotton cretonne is impregnated with liquors of the following composition:

| | | |
|---|---|---|
| (A) | 100 g of the polymer of Example 12, 13, 15, 16 or 17, | |
| | 900 g of dioxane, and | |
| | 0.01 g of a sensitiser. | |
| (B) | 100 g of the polymer of Example 12, 13, 15, 16 or 17 | |
| | 900 g of dioxane, | |
| | 0.01 g of a sensitiser and | |
| | 0.05 g of a photoinitiator. | |

The fabric is pinched-off to a pick-up of 100% and then dried for 4 hours at 60° C.

The treated cretonne samples are then tested for their textile finishing properties by:
(a) extracting the samples twice with dioxane,
(b) irradiating the fabric with a 5000 W Staub UV lamp (W. Staub GmbH, Neu-Isenburg, Germany) at a distance of 80 cm for 5 minutes on one side, and
(c) irradiating the fabric as in (b) and then extracting the samples twice with dioxane and subsequently determining the $N_2$ content in %.

The results are reported in Table V.

TABLE V

| Polymer of Example | Liquor | dried extracted $N_2$* (%) | dried irradiated with UV light $N_2$* (%) | dried irradiated with UV light extracted $N_2$* (%) |
|---|---|---|---|---|
| 12** | A | 0.01 | 1.06 | 0.42 |
| | B | 0.02 | 0.96 | 0.43 |
| 13 | A | 0.51 | 1.06 | 1.08 |
| | B | 0.41 | 1.12 | 0.89 |
| 15 | A | 0.71 | 1.26 | 0.79 |
| | B | 0.73 | 1.21 | 1.02 |
| 16 | A | 0.04 | 1.16 | 0.92 |
| | B | 0.02 | 1.16 | 0.96 |
| 17 | A | 0.05 | 0.94 | 0.75 |
| | B | 0.05 | 0.97 | 0.88 |

*Elemental analysis
**This sample was not extracted, but washed at a liquor ratio of 1:40 for 30 minutes at 95° C. in a liquor containing 5 g/l of soap and 2 g/l of sodium carbonate, and then dried.

Example 23

A 33/67 cotton/Diolen ® blend (210 g/m²) is impregnated with a liquor containing

| |
|---|
| 50 g of the polymer of Example 18, |
| 950 g of the dioxane, and |
| 0.01 g of a sensitiser, | pinched-off to a pick-up of 80%, and then dried at 60° C. The treated, dried fabric is then irradiated on both sides as described in Example 22 and subsequently extracted twice with dioxane in order to remove nonreacted polymer. A sample measuring 20×25 cm is conditioned at 20° C. and 65% relative humidity and weighed (weight A) and then subjected to the spray test by fixing it between two clamps and spraying it with 500 ml of water of 20° C. The sample is then stretched vigorously three times lengthways to free it from drops. The sample is then held lengthways and crosswise, shaken vigorously three times in each position and weighed (weight B). The amount of water absorbed is then determined from these weights (amount of water in % =

TABLE VI

| Sample | Water absorption in % |
|---|---|
| non-finished | 92.3 |
| finished and irradiated | 23.1 |
| finished but not irradiated | 79.8 |

The same test is carried out using a non-finished sample and a sample which has been finished but not irradiated.

The results are reported in table VI.

| |
|---|
| 50 g of polymer of Example 14, |
| 950 g of dioxan, and |
| 0.01 g of a sensitiser, |

Example 24

A cotton cretonne fabric (135 g/m²) is impregnated with a liquor containing $$\left(\text{amount of water in \%} = \frac{B - A}{A} \cdot 100\right).$$

pinched-off to a pick-up of 85% and subsequently dried at 60° C. The treated, dry fabric is then irradiated on both sides as described in Example 22 and then extracted twice with dioxane to remove any nonreacted polymer.

The flexural strength of this fabric is determined in accordance with ASTM D 1388-64 T.

The same test is carried out with a non-finished sample and with a sample which has been finished but not irradiated.

The results are reported in Table VII.

TABLE VII

| Sample | Flexural strength* |
|---|---|
| non-finished | 457 |
| finished and irradiated | 6487 |
| finished but not irradiated | 630 |

*The higher the number, the stiffer the sample.

Example 25

The procedure of Example 23 is repeated, using a 33/67 cotton/polyester blend (290 g/m$^2$) and a liquor containing

| | |
|---|---|
| 100 g | of the polymer of Example 18, |
| 900 g | of dioxane, and |
| 0.02 g | of a sensitiser. |

The treated fabric is then tested for its impermeability to water in accordance with DIN 53 886.

The same test is carried out with a non-finished sample and a sample which has been finished but not irradiated. The water impermeability is expressed in cm water column.

The results are reported in Table VIII.

TABLE VIII

| Sample | Water column (cm) |
|---|---|
| non-finished | 0 |
| finished and irradiated | 13 |
| finished but not irradiated | 0 |

What is claimed is:

1. A N-alkenoyl enamide of the formula $$R_1CH=CR_2-CO-NH-CH=C\begin{matrix}R_3\\R_4\end{matrix}$$

wherein
$R_1$ is hydrogen or methyl,
$R_2$ is hydrogen, $C_1$–$C_4$alkyl or halogen, and at least one of
$R_3$ and $R_4$ is CO—$R_5$, benzoyl, phenyl or cyano, wherein
$R_5$ is $C_1$–$C_4$alkyl and
$R_4$ can also be hydrogen.

2. An N-alkenoyl enamide according to claim 1, wherein $R_2$ is hydrogen, methyl or chlorine, and at least one of $R_3$ and $R_4$ is acetyl, benzoyl, phenyl or cyano and $R_4$ can also be hydrogen.

3. An N-alkenoyl enamide according to claim 1, wherein $R_2$ is hydrogen or methyl, and $R_3$ and $R_4$ are each acetyl.

4. A compound of claim 1 wherein at least one of $R_3$ and $R_4$ is —CO—$R_5$ or benzoyl wherein $R_5$ is $C_1$–$C_4$alkyl and $R_4$ can also be hydrogen.

* * * * *